United States Patent [19]

Kallenberger

[11] 4,256,720
[45] Mar. 17, 1981

[54] METHOD FOR PRODUCING CARBON BLACK

[75] Inventor: Robert H. Kallenberger, Bartlesville, Okla.

[73] Assignee: Phillips Petroleum Company, Bartlesville, Okla.

[21] Appl. No.: 19,947

[22] Filed: Mar. 12, 1979

[51] Int. Cl.$^3$ .......................... C01B 31/02; C09C 1/48
[52] U.S. Cl. .................... 423/449; 423/450; 423/DIG. 5; 422/62; 422/150; 23/230 A
[58] Field of Search .............. 423/445, 449, 450, 460, 423/461, DIG. 5; 422/62, 150; 23/230 A

[56] References Cited

U.S. PATENT DOCUMENTS

| | | | |
|---|---|---|---|
| 3,135,277 | 6/1964 | Lutter | 137/3 |
| 3,482,327 | 12/1969 | Dutcher | 34/12 |
| 3,993,447 | 11/1976 | Buss et al. | 423/450 |
| 4,080,434 | 3/1978 | Buss et al. | 423/450 |

Primary Examiner—O. R. Vertiz
Assistant Examiner—Gregory A. Heller

[57] ABSTRACT

In a carbon black manufacturing process in which an off-specification rerun carbon black is mixed with the carbon black flowing from a carbon black reactor to produce a combined carbon black stream, method and apparatus is provided for controlling the carbon black process so as to insure that the combined carbon black stream will meet predetermined specifications. The feed flow to the carbon black reactor is controlled in response to a comparison of a prediction of the actual surface area of the combined carbon black stream with the desired surface area of the combined carbon black stream so as to provide a combined carbon black stream made up of carbon black particles which have a desired surface area. The flow of potassium to the carbon black reactor is controlled in response to a comparison of a prediction of the structure of the combined carbon black stream with the desired structure for the combined carbon black stream so as to produce a combined carbon black stream in which the aggregated carbon black particles have a desired structure.

15 Claims, 2 Drawing Figures

METHOD FOR PRODUCING CARBON BLACK

This invention relates generally to carbon black production. In a particular aspect this invention relates to method and apparatus for controlling a carbon black process so as to produce carbon black which meets predetermined specifications when rerun carbon black which does not meet the predetermined specifications is mixed with the carbon black flowing from the carbon black reactor.

There are numerous tests which can be utilized to ascertain various properties of carbon black. Two of these tests, which are of particular interest in the present invention, are the cetyltrimethylammonium bromide (CTAB) test and the dibutyl phthalate (DBP) absorption test. The CTAB number is a measurement of the surface area of the carbon black particles. The DBP number is a measurement of the structure of the aggregated carbon black particles. Both the CTAB test and the DBP test are well known. The CTAB test is disclosed in *Specific Surface Area Measurements On Carbon Black* by J. Janzen and G. Kraus, Rubber Chemistry and Technology, Vol. 44, P 1287, 1971. The DBP test is a standard ASTM test D 4414-76.

Carbon black processes periodically produce carbon black which does not meet predetermined specifications for the CTAB number or DBP number. This off-specification carbon black (rerun carbon black) can often be blended with carbon black flowing from a carbon black reactor (production carbon black) with the resultant combined carbon black stream (product carbon black) meeting predetermined specifications. However, it is not possible to measure the flow rate or meter the off-specification rerun carbon black or the production carbon black flowing from the carbon black reactor. Because of this, the compensation for the off-specification properties of the rerun carbon black is currently accomplished by trial and error which may produce off-specification product carbon black again which is highly undesirable.

It is thus an object of this invention to provide method and apparatus for controlling a carbon black process so as to produce carbon black which meets predetermined specifications when rerun carbon black which does not meet the predetermined specifications is mixed with production carbon black flowing from a carbon black reactor.

In accordance with the present invention, method and apparatus is provided whereby the flow of the feed to the carbon black reactor is controlled so as to maintain a desired CTAB number for the particles of the combined carbon black stream containing the off-specification rerun carbon black and the production carbon black. The flow rate of potassium to the carbon black reactor is controlled so as to maintain a desired DBP number for the aggregated particles contained in the combined carbon black stream. In this manner, a product carbon black stream which meets predetermined specifications can be produced from the combination of production carbon black and off-specification rerun carbon black.

The flow rate of the feed flowing to the carbon black reactor is controlled by calculating the number of pounds of carbon black being produced per hour by the carbon black reactor. Based on the calculated number of pounds of carbon black being produced per hour by the carbon black reactor, the measured flow rate of water to the carbon black mixer and the percentage of water on the carbon black flowing from the mixer, the number of pounds of rerun carbon black being added per hour to the production carbon black is calculated. The predicted CTAB number for the particles of the product carbon black stream is calculated based on the flow rate of the production carbon black, the flow rate of the rerun carbon black, the predicted CTAB number of the particles of the production carbon black stream and the measured CTAB number of the particles of the rerun carbon black stream. The predicted CTAB number of the product carbon black stream is compared to the desired CTAB number of the particles of the product carbon black stream and the flow rate of the feed to the carbon black reactor is controlled in response to this comparison so as to maintain the actual CTAB number of the particles of the combined carbon black stream substantially equal to the desired CTAB number for the particles of the combined carbon black stream.

The flow rate of the potassium to the carbon black reactor is controlled by calculating the predicted DBP number of the aggregated particles of the production carbon black stream. This predicted value is combined with a measured DBP number for the aggregated particles of the rerun carbon black stream to provide a calculation of the actual DBP number of the aggregated particles of the product carbon black stream. The calculated DBP number of the aggregated particles of the product carbon black stream is compared to the desired DBP number of the aggregated particles of the product carbon black stream and the flow rate of potassium to the carbon black reactor is controlled in response to this comparison so as to maintain the DBP number of the aggregated particles of the product carbon black stream substantially equal to the desired DBP number for the aggregated particles of the product carbon black stream. Other objects and advantages of the invention will be apparent from the foregoing description of the invention and the appended claims as well as from the detailed description of the drawings in which:

For the sake of simplicity, the invention is illustrated and described in terms of a single carbon black reactor having a single reaction chamber. The invention, however, is applicable to multiple carbon black reactors and is also applicable to carbon black reactors having multiple combustion chambers.

The invention is described in terms of a carbon black process in which air is utilized as the oxygen-containing gas and water is utilized as the carbon black binding agent. The invention is, however, applicable to carbon black processes which use fluids other than air to supply oxygen and which use binding agents other than water.

Although the invention is illustrated and described in terms of a specific carbon black reactor and a specific control configuration, the applicability of the invention described herein extends to other types of carbon black reactors and also extends to different types of control system configurations which accomplish the purpose of the present invention. Lines designated as signal lines in the drawings are electrical in this preferred embodiment. However, the invention is also applicable to pneumatic, mechanical, hydraulic, or other signal means for transmitting information. In almost all control systems some combination of these types of signals will be used. However, use of any other type of signal transmission, compatible with the process and equipment in use, is within the scope of the invention.

Both the analog and digital controllers shown may utilize the various modes of control such as proportional, proportional-integral, proportional-derivative, or proportional-integral-derivative. In this preferred embodiment, proportional-integral controllers are utilized but any controller capable of accepting two input signals and producing a scaled output signal, representative of a comparison of the two input signals, is within the scope of the invention. The operation of proportional-integral controllers is well known in the art. The output control signal of a proportional-integral controller may be represented as $$S = K_1 E + K_2 \int E dt$$

where
S = output control signals;
E = difference between two input signals; and
$K_1$ and $K_2$ = constants.

The scaling of an output signal by a controller is well known in control systems art. Essentially, the output of a controller may be scaled to represent any desired factor or variable. An example of this is where a desired pressure and an actual pressure is compared by a controller. The output could be a signal representative of a desired change in the flow rate of some gas necessary to make the desired and actual pressures equal. On the other hand, the same output signal could be scaled to represent a percentage or could be scaled to represent a temperature change required to make the desired and actual pressures equal. If the controller output can range from 0 to 10 volts, which is typical, then the output signal could be scaled so that an output signal having a voltage level of 5.0 volts corresponds to 50 percent, some specified flow rate, or some specified temperature.

The various transducing means used to measure parameters which characterize the process and the various signals generated thereby may take a variety of forms or formats. For example, the control elements of the system can be implemented utilizing electrical analog, digital electronic, pneumatic, hydraulic, mechanical or other similar types of equipment or combinations of the invention preferably utilizes a combination of one or more of such equipment types. While the presently preferred embodiment of pneumatic control elements, electrical analog signal handling and translation apparatus, and a digital computer, the apparatus and method of the invention can be implemented using a variety of specific equipment available to and understood by those skilled in the process control art. Likewise, the format of the various signals can be modified substantially in order to accommodate signal format requirements of the particular installation, safety factors, the physical characteristics of the measuring or control instruments and other similar factors. For example, a raw flow measurement signal produced by a differential pressure orifice flow meter would ordinarily exhibit a generally proportional relationship to the square of the actual flow rate. Other measuring instruments might produce a signal which is proportional to the measured parameter, and still other measuring instruments may produce a signal which bears a more complicated, but known, relationship to the measured parameter. In addition, all signals could be translated into a "suppressed zero" or other similar format in order to provide a "live zero" and prevent an equipment failure from being erroneously interpreted as a low (or high) measurement or control signal. Regardless of the signal format or the exact relationship of the signal to the parameter which it represents, each signal representative of a measured process parameter or representative of a desired process value will bear a relationship to the measured parameter or desired value which permits designation of a specific measured or desired value by a specific signal value. A signal which is representative of a process measurement or desired process value is therefore one from which the information regarding the measured or desired value can be readily retrieved regardless of the exact mathematical relationship between the signal units and the measured or desired process units.

Figure 1:
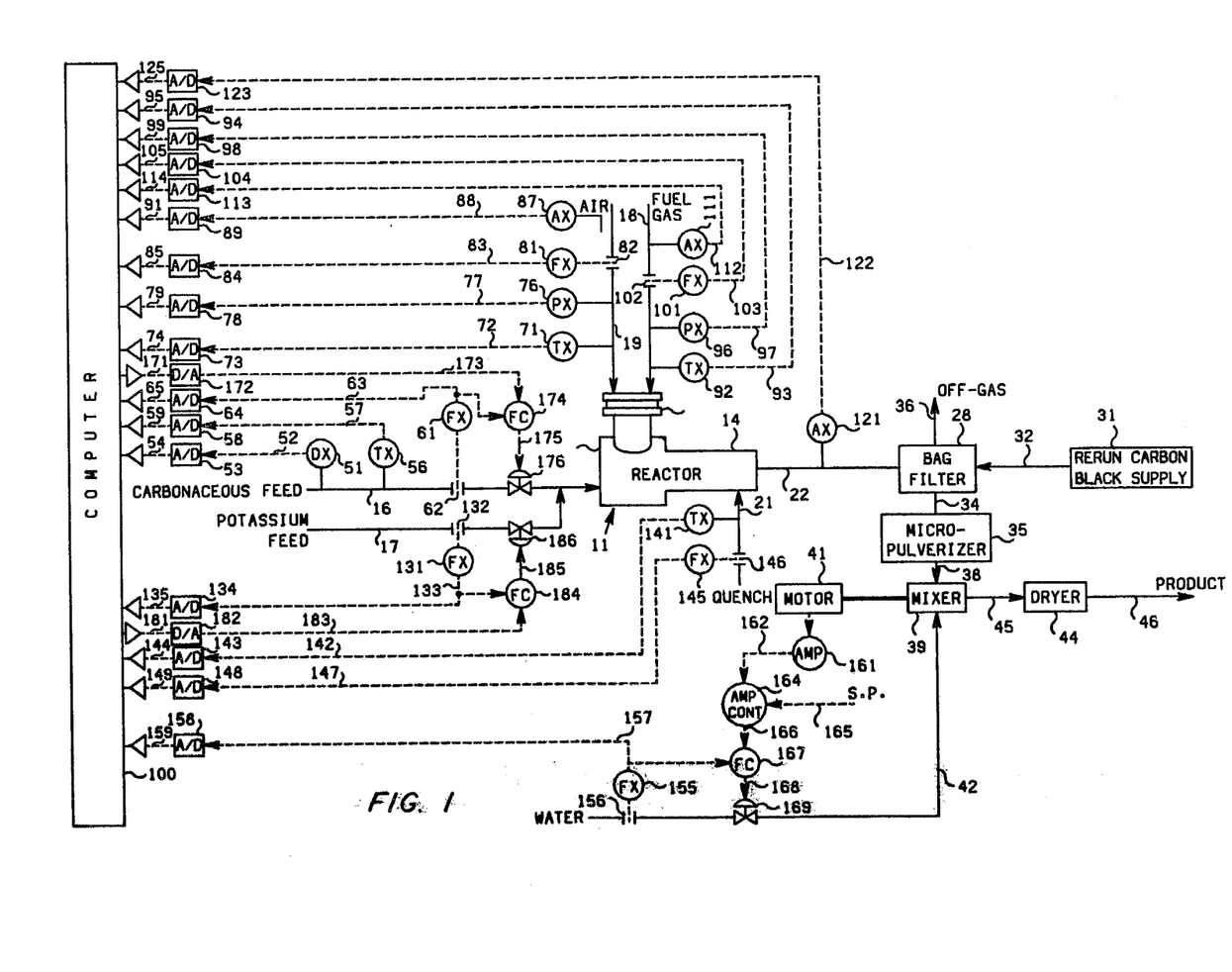
FIG. 1 is a schematic representation of the apparatus used for producing carbon black in the present invention together with the associated control system for the carbon black process.

Referring now to the drawings and in particular to FIG. 1, a carbon black reactor 11 having a combustion tunnel 12, combustion or precombustion chamber 13, and a reaction chamber 14 is illustrated. A carbonaceous feed is supplied to the carbon black precombustion chamber 13 through conduit means 16 although the carbonaceous feed may be supplied directly to the reaction chamber 14 if desired. A potassium containing feed such as an aqueous solution of potassium nitrate (KNO3) is supplied to the carbon black precombustion chamber 13 through conduit means 17. Fuel gas is supplied to the carbon black combustion tunnel 12 through conduit means 18. Air is supplied to the carbon black combustion tunnel 12 through conduit means 19. The hot combustion gases produced in the carbon black combustion tunnel 12 are introduced into the carbon black precombustion chamber 13 preferably in a generally tangential manner, with respect to the carbon black reaction chamber 14, so as to effect a vortex flow of the hot combustion gases along the length of the carbon black reaction chamber 14. The hot combustion gases introduced from the carbon black combustion tunnel 12 contact the carbonaceous feed at a temperature sufficiently high to pyrolyze a substantial portion of the carbonaceous feed to carbon black particles. After a predetermined length of reaction time, depending mainly on desired photelometer, the effluent flowing through the reaction chamber 14 is quenched by contact with a quench fluid which is introduced into reaction chamber 14 through conduit means 21. Water, cool smoke or other similar fluids can be used as the quench fluid.

The effluent from the carbon black reaction chamber 14, which contains the carbon black particles (production carbon black) and other gases is supplied through conduit means 22 to the filter 28 which is preferably a bag filter. The filter 28 is utilized to separate the carbon black particles from the gaseous portion of the effluent flowing from the reactor 14.

Rerun carbon black is provided from the rerun carbon black supply 31 to the bag filter 28 through conduit means 32. The rerun carbon black supply 31 may be a hopper or other similar storage bin which contains off-specification carbon black which was produced previously. Off-specification carbon black is combined with the production carbon black flowing from the reaction chamber 14 and the combined product carbon black stream is provided through conduit means 34 to the micropulverizer 35. Off-gas from the bag filter 28 flows from the bag filter 28 through conduit means 36.

From the micropulverizer 35 the product carbon black stream is provided through conduit means 38 to the mixer 39 which is driven by the motor 41. The mixer 39 is also provided with a flow of water through conduit means 42. The product carbon black stream is pelletized in the mixer 39 and is provided to the carbon black pellet dryer 44 through conduit means 45. The dried carbon black is provided as product from the carbon black pellet dryer 44 through conduit means 46.

The carbon black process described to this point is a conventional process for manufacturing carbon black. It is the manner in which a carbon black production process is controlled so as to maintain a desired specification for the carbon black product flowing through conduit means 46 which provides the novel features of the present invention.

The density meter 51 provides an output signal 52 which is representative of the density of the feed flowing through conduit means 16. Signal 52 is provided from the density meter 51 as an input to the analog-to-digital (A/D) converter 53. Signal 52 is converted from analog form to digital form and is provided as signal 54 to computer means 100. Temperature transducer 56, in combination with a temperature measuring device such as a thermocouple which is operably located in conduit means 16, provides an output signal 57 which is representative of the temperature of the feed flowing through conduit means 16. Signal 57 is provided from the temperature transducer 56 as an input to the A/D converter 58. Signal 57 is converted from analog form to digital form and is provided as signal 59 to computer means 100. The flow transducer 61, in combination with the flow sensor 62, provides an output signal 63 which is representative of the flow rate of the feed flowing through conduit means 16. Signal 63 is provided from the flow transducer 61 as an input to the A/D converter 64. Signal 63 is converted from analog form to digital form and is provided as signal 65 to computer means 100.

The temperature transducer 71, in combination with a temperature measuring device such as a thermocouple which is operably located in conduit means 19, provides an output signal 72 which is representative of the temperature of the air flowing through conduit means 19. Signal 72 is provided as an input to the A/D converter 73. Signal 72 is converted from analog form to digital form and is provided as signal 74 to computer means 100. The pressure transducer 76, which is operably connected to conduit means 19, provides an output signal 77 which is representative of the pressure of the air flowing through conduit means 19. Signal 77 is provided as an input to the A/D converter 78. Signal 77 is converted from analog form to digital form and is provided as signal 79 to computer means 100. The flow transducer 81, in combination with the flow sensor 82, provides an output signal 83 which is representative of the flow rate of the air flowing through conduit means 19. Signal 83 is provided as an input to the A/D converter 84. Signal 83 is converted from analog form to digital form and is provided as signal 85 to computer means 100. Analyzer transducer 87, provides an output signal 88 which is representative of the dew point of the ambient air and thus representative of the dew point of the air flowing through conduit means 19. Signal 88 is provided as an input to the A/D converter 89. Signal 88 is converted from analog form to digital form and is provided as signal 91 to computer means 100.

Temperature transducer 92, in combination with a temperature measuring device such as a thermocouple which is operably located in conduit means 18, provides an output signal 93 which is representative of the flow rate of the fuel gas flowing through conduit means 18. Signal 93 is provided as an input to the A/D converter 94. Signal 93 is converted from analog form to digital form and is provided as signal 95 to computer means 100. Pressure transducer 96, which is operably connected to conduit means 18, provides an output signal 97 which is representative of the pressure of the fuel gas flowing through conduit means 18. Signal 97 is provided as an input to the A/D converter 98. Signal 97 is converted from analog form to digital form and is provided as signal 99 to computer means 100. Flow transducer 101, in combination with the flow sensor 102, provides an output signal 103 which is representative of the flow rate of the fuel gas flowing through conduit means 18. Signal 103 is provided as an input to the A/D converter 104. Signal 103 is converted from analog form to digital form and is provided as signal 105 to computer means 100. The analyzer transducer 111, which is preferably a chromatographic analyzer, is operably connected to conduit means 18. The analyzer transducer 111 provides a plurality of output signals which are represented by signal 112. The plurality of output signals, which are represented by signal 112, are respectively representative of the concentration of nitrogen, carbon dioxide, methane, ethane, propane and butane in the fuel gas flowing through conduit means 18. The plurality of signals, which are representated by signal 112, are provided to a plurality of A/D converters, which are represented by A/D converter 113. The plurality of signals, which are represented by signal 112, are converted from analog form to digital form and are provided as a plurality of signals, which are represented by signal 114 to computer means 100.

Analyzer transducer 121, which is preferably a chromatographic analyzer, is operably connected to conduit means 22. The analyzer transducer 121 provides a plurality of output signals which are represented by signal 122. The plurality of output signals, which are represented by signal 122, are respectively representative of the concentration of acetylene, hydrogen, nitrogen, carbon dioxide, carbon monoxide, and methane in the effluent flowing through conduit means 22. The plurality of signals, of which signal 122 is representative, are provided to a plurality of A/D converters of which A/D converter 123 is representative. The plurality of signals, of which signal 122 is representative, are converted from analog form to digital form and are provided as a plurality of signals, represented by signal 125, to computer means 100.

Flow transducer 131, in combination with the flow sensor 132, provides an output signal 133 which is representative of the flow rate of the potassium containing feed flowing through conduit means 17. Signal 133 is provided as an input to the A/D converter 134. Signal 133 is converted from analog form to digital form and is provided as signal 135 to computer means 100.

Temperature transducer 141, in combination with a temperature measuring device such as a thermocouple which is operably located in conduit means 21, provides an output signal 142 which is representative of the temperature of the quench fluid flowing through conduit means 21. Signal 142 is provided as an input to the A/D converter 143. Signal 142 is converted from analog form to digital form and is provided as signal 144 to computer means 100. The flow transducer 145, in combination with the flow sensor 146, provides an output signal 147 which is representative of the flow rate of the quench fluid flowing through conduit means 21. Signal 147 is provided as an input to the A/D converter 148. Signal 147 is converted from analog form to digital form and is provided as signal 149 to computer means 100.

Flow transducer 155, in combination with the flow sensor 156, provides an output signal 157 which is representative of the flow rate of the water flowing through conduit means 42. Signal 157 is provided as an input to the A/D converter 158. Signal 157 is converted from analog form to digital form and is provided as signal 159 to computer means 100.

The ammeter 161 provides an output signal 162 which is representative of the electrical current being drawn by the motor 41. Signal 162 is provided as a first input to the current controller 164. The current controller 162 is also provided with a set point input 165 which is representative of the desired electrical current to be drawn by the motor 41. The current controller 164 compares signals 62 and 65 and provides an output signal 166 which is responsive to the difference between signals 162 and 165. Signal 166 is provided as a first input to the flow controller 167. Signal 166 is scaled so as to be representative of the desired flow rate of the water flowing through conduit means 42 which will provide a desired loading for the motor 41. The flow controller 167 is also provided with signal 157 which is representative of the actual flow rate of the water flowing through conduit means 42. The flow controller 167 compares signals 157 and 166 and provides an output signal 168 which is responsive to the difference between signals 157 and 166. Signal 168 is provided as an input to the pneumatic control valve 169. The pneumatic control valve 169 is manipulated in response to signal 168 so as to provide a flow rate of binding fluid through conduit means 42 which will provide a desired loading for the motor 41.

In response to the described input signals, and in response to a plurality of manual input signals which will be described hereinafter, the computer means 100 generates two output signals 171 and 181. Signal 171 is representative of the flow rate of the feed flowing through conduit means 16 which will maintain a desired CTAB number for the particles in the carbon black product flowing through conduit means 46. Signal 171 is provided as an input to the D/A converter 172. Signal 171 is converted from digital form to analog form and is provided as signal 173 to the flow controller 174. The flow controller 174 is also provided with signal 63 which is representative of the actual flow rate of the feed flowing through conduit means 16. The flow controller 174 compares signals 63 and 173 and provides an output signal 175 which is responsive to the difference between signals 63 and 173. Signal 175 is provided as a control signal to the pneumatic control valve 176 which is operably located in conduit means 16. The pneumatic control valve 176 is manipulated in response to signal 175 so as to maintain a desired flow rate for the feed flowing through conduit means 16.

Signal 181 is representative of the flow rate of the potassium containing feed which is required to maintain a desired DBP number for the aggregated carbon black particles in the carbon black product flowing through conduit means 46. Signal 181 is provided as an input to the D/A converter 182. Signal 181 is converted from digital form to analog form and is provided as signal 183 to the flow controller 184. The flow controller 184 is also provided with signal 133 which is representative of the actual flow rate of potassium containing feed flowing through conduit means 17. The flow controller 184 compares signals 133 and 183 and provides an output signal 185 which is responsive to the difference between signals 133 and 183. Signal 185 is provided as a control signal to the pneumatic control valve 186 which is operably located in conduit means 17. The pneumatic control valve 186 is manipulated in response to signal 185 to provide a desired flow rate of the potassium containing feed through conduit means 17.

Figure 2:
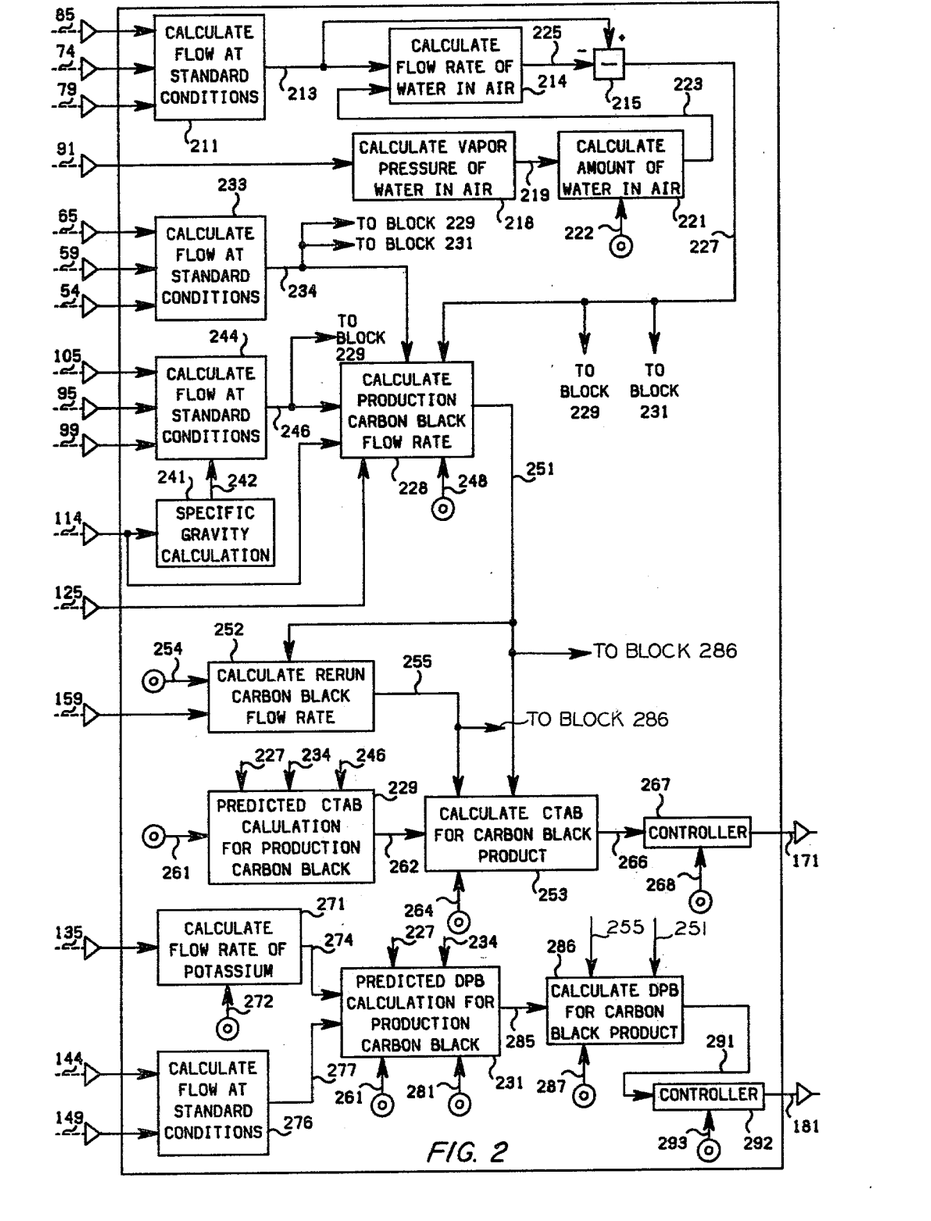
FIG. 2 is a schematic representation of the computer logic utilized to process the measured data provided to the computer to provide the set points required by the control system illustrated in FIG. 1.

FIG. 2 illustrates a flow diagram for the computer logic utilized to implement the control system illustrated in FIG. 1. As is illustrated in FIG. 2, signals 85, 74 and 79 which are representative of the measured flow rate, the measured pressure and the measured temperature, respectively, of the air flowing through conduit means 19 are supplied to the calculate flow at standard conditions block 211. Signals 85, 74 and 79 are utilized to calculate the flow rate of the air flowing through conduit means 19 at standard conditions utilizing equation (I):

$$F_A = (F_{MEAS}) \left( \sqrt{\frac{T_{STD}}{T_{MEAS}}} \right) \left( \sqrt{\frac{P_{MEAS}}{P_{STD}}} \right) \quad (I)$$

where
 $F_A$ = flow rate of air at standard conditions;
 $F_{MEAS}$ = measured flow rate;
 $T_{STD}$ = standard temperature;
 $T_{MEAS}$ = measured temperature;
 $P_{STD}$ = standard pressure; and
 $P_{MEAS}$ = measured pressure.

Signal 213, which is representative of the flow rate of the air flowing through conduit means 19 at standard conditions, is supplied from the calculate flow at standard conditions block 211 as an input to the calculate flow rate of water in air block 214 and as an input to the subtracting block 215.

Signal 91, which is representative of the dew point temperature of the air flowing through conduit means 19, is provided as an input to the calculate vapor pressure of water in air block 218. Signal 91 is utilized to calculate the vapor pressure of the water in the air utilizing equation (II):

(II) $PW = 10^{[A + (B)(T) + C/(T+D)]}$ where
 PW = vapor pressure of water in the air flowing through conduit means 19;
 T = dew point temperature of the air flowing through conduit means 19; and
 A, B, C, and D are constants.

In the range of -30° to 115° F., preferred values for the constants A, B, C, and D are as follows:
 A = 5.3193480
 B = -0.00058601588
 C = -2119.6319
 D = 3.0100159

Signal 219, which is representative of the vapor pressure of the water in the air flowing through conduit means 19, is provided from the calculate vapor pressure water in air block 218 as an input to the calculate amount of water in air block 221. The calculate amount of water in air block 221 is also provided with a set point signal 222 which is representative of the barometric pressure at the carbon black manufacturing site. Signals 219 and 222 are utilized to calculate the pounds of water per pound of air in the air flowing through conduit means 19 utilizing equation (III):

$$WT = \frac{PW}{PB - PW} \frac{18.016}{28.97} \qquad (III)$$

where
- $WT$ = pounds of water/pounds of air in the air flowing to conduit means 19;
- $PW$ = vapor pressure of the water in the air flowing to conduit means 19; and
- $PB$ = barometric pressure.

Signal 223, which is representative of the pounds of water per pound of air in the air flowing through conduit means 19, is provided from the calculate amount of water in air block 221 as an input to the calculate flow rate of water in air block 214. Signals 213 and 223 are utilized to calculate the flow rate of the water in the air flowing through conduit means 19 utilizing equation (IV):

$$F_{WATER} = (F_A)(WT) \qquad (IV)$$

where
- $F_{WATER}$ = flow rate of water in the air flowing through conduit means 19;
- $F_A$ = flow rate of the air containing water flowing through conduit means 19; and
- $WT$ is as previously defined.

Signal 225, which is representative of the flow rate of the water in the air flowing through conduit means 19, is provided from the calculate flow rate of water in air block 214 to the subtracting block 215. Signal 225 is subtracted from signal 213 to provide signal 227 which is representative of the flow rate of dry air flowing through conduit means 19. Signal 227 is provided as an input to the calculate production carbon black flow rate block 228, as an input to the predicted CTAB calculation for production carbon black block 229 and as an input to the predicted DPB calculation for production carbon black block 231.

Signals 65, 59 and 54 which are respectively representative of the flow rate, temperature and density of the feed flowing through conduit means 16 are provided as inputs to the calculate flow at standard conditions block 233. Signals 65, 59 and 54 are utilized to calculate the flow rate of the feed flowing through conduit means 16 at standard conditions utilizing equation (V):

$$F_F = (F_{MEAS}) \left( \sqrt{\frac{T_{STD}}{T_{MEAS}}} \right) \left( \sqrt{\frac{1}{D}} \right) \qquad (V)$$

where
- $F_F$ = flow rate of feed at standard conditions;
- $D$ = density of the feed flowing through conduit means 16; and
- $F_{MEAS}$, $T_{STD}$ and $T_{MEAS}$ are as previously defined.

Signal 234, which is representative of the flow rate of the feed flowing through conduit means 16 at standard conditions, is provided as an input to the calculate production carbon black flow rate block 228, as an input to the predicted CTAB calculation for production carbon black block 229 and as an input to the predicted DBP calculation for production carbon black 231.

Signal 114, which is representative of the plurality of signals which are provided from the analyzer transducer 111, is provided as an input to the specific gravity calculation block 241 and as an input to the calculate production carbon black flow rate block 228. The mol percent of each constituent is multiplied by the specific gravity of each constituent and the results are summed in the specific gravity calculation block 241 to provide signal 242 which is representative of the specific gravity of the fuel gas flowing through conduit means 18. Equation (VI) is utilized in the specific gravity calculation to provide signal 242:

$$SG_F = \sum_{i=\text{nitrogen}}^{\text{butane}} (\text{mol \%}) (SG_i) \qquad (VI)$$

where
- $SG_F$ = specific gravity of the fuel gas flowing through conduit means 18;
- mol $\%_i$ = mol % of a specific component in the feed stream;
- $SG_i$ = specific gravity of a specific component in the fuel gas flowing through conduit means 18; and
- $i$ is the particular constituent in the fuel gas (nitrogen, carbon dioxide, methane, ethane, propane, and butane).

Signal 242 is provided from the specific gravity calculation block 241 as an input to the calculate flow at standard conditions block 244.

Signals 105, 95 and 99, which are respectively representative of the flow rate, temperature, and pressure of the fuel gas flowing through conduit means 18, are provided as inputs to the calculate flow at standard conditions block 244. Signals 105, 95, 99 and 242 are utilized to calculate the flow rate of the fuel gas ($F_G$) flowing through conduit means 18 at standard conditions utilizing equation (VII):

$$F_G = (F_{MEAS}) \left( \sqrt{\frac{T_{STD}}{T_{MEAS}}} \right) \left( \sqrt{\frac{P_{MEAS}}{P_{STD}}} \right) \left( \sqrt{\frac{1}{SG_F}} \right) \qquad (VII)$$

where $F_{MEAS}$, $T_{STD}$, $T_{MEAS}$, $P_{MEAS}$, $P_{STD}$ and $SG_F$ are as previously defined.

Signal 246, which is representative of the flow rate of the fuel gas flowing through conduit means 18 at standard conditions, is provided as an input to the calculate production carbon black flow rate block 228 and also is an input to the predicted CTAB calculation for production carbon black block 229.

Signal 125, which is representative of the plurality of outputs which are provided from the analyzer transducer 121 is provided as an input to the calculate production carbon black flow rate block 228. The calculate production carbon black flow rate block 228 is also provided with set point signal 248. Signal 248 is representative of the percentage of carbon in the feed flowing through conduit means 16. Signal 248 is derived from a laboratory analysis of the feed flowing through conduit means 16. The latest laboratory analysis available for the feed flowing through conduit means 16 is utilized for the set point signal 248.

All of the flow rates into the carbon black reactor in combination with the analysis of the carbon containing flows to the carbon black reactor are utilized in a material balance to produce signal 251 which is representative of the flow rate of carbon black out of the reactor 11 $F_{PC}$. As has been previously stated, this flow rate cannot be measured and it is thus necessary to utilize a material balance to derive the flow rate of the carbon black. Specifically, the flow rate of carbon containing materials other than carbon black out of the reactor 11 is subtracted from the flow rate of carbon into the reactor 11 to produce signal 251 which is representative of the flow rate of the production carbon black out of the reactor 11. Signal 251 is provided from the calculate production carbon black flow rate block 228 as an input to the calculate rerun carbon black flow rate block 252, as an input to the calculate CTAB for carbon black product block 253 and as an input to the calculate DBP for carbon black product block 286.

Signal 159, which is representative of the flow rate of the water flowing through conduit means 42, is provided as an input to the calculate rerun carbon black flow rate block 252. The set point signal 254, which is a representative of the percentage of water in the carbon black flowing from the mixer 39, is also provided to the calculate rerun carbon black flow rate block 252. Signal 254 is obtained from a laboratory analysis of the carbon black flowing from the mixer 39. Signals 251, 254 and 159 are utilized to calculate the flow rate of the rerun carbon black utilizing equation. (VIII):

$$F_{RC} = (F_W)(WT\%_W) - F_{PC} \quad \text{(VIII)}$$

where $F_{RC}$ = flow rate of the rerun carbon black;
$F_W$ = flow rate of the water flowing to the mixer 39;
$WT\%_W$ = weight % of water in the carbon black flowing out of the mixer 39; and
$F_{PC}$ = flow rate of the production carbon black.

Signal 255, which is representative of the flow rate of the rerun carbon black ($F_{RC}$), is provided from the calculate rerun carbon black flow rate block 252 as an input to the calculate CTAB for carbon black product block 253 and as an input to the calculate DBP for carbon black product block 286.

Signal 261, which is representative of the length of the carbon black reactor 11, is provided as an input to the predicted CTAB calculation for production carbon black 229. Signals 227, 234, 246 and 261 are utilized to provide a prediction of the CTAB number for the production carbon black utilizing equation (IX):

$$CTAB_P = a + (b)(F_A) + (c)(F_G) + (d)(F_F) + (e)(L) \quad \text{(IX)}$$

where $CTAB_p$ = predicted CTAB number for the production carbon black;
$L$ = length of the reactor;
$a, b, c, d$ and $e$ = constants; and
$F_A, F_G$ and $F_F$ are as previously defined.

The constants a, b, c, d and e are determined by making a test run in which the CTAB number for the production carbon black is determined by a laboratory analysis. Based on the laboratory value for the CTAB number, the constants a, b, c, d and e are determined by a linear regression analysis. Signal 262, which is representative of the predicted CTAB number for the production carbon black, is provided from the predicted CTAB calculation for production carbon black block 229 as an input to the calculate CTAB for carbon black product block 253.

Signal 264, which is representative of the measured CTAB number for the rerun carbon black (CTAB) is provided as an input to the calculate CTAB for carbon black product block 253. Signal 264 is obtained from a laboratory analysis of the rerun carbon black. Signals 255, 253, 262 and 264 are utilized to calculate the CTAB number for the carbon black product flowing out of conduit means 46 utilizing equation (X):

$$CTAB_{PROD} = \left(\frac{F_{RC}}{F_{RC} + F_{PC}}\right)(CTAB_R) + \left(\frac{F_{PC}}{F_{RC} + F_{PC}}\right)(CTAB_P) \quad \text{(X)}$$

where $CTAB_{PROD}$ = CTAB number of the product carbon black; and
$F_{RC}$, $CTAB_R$, $F_{PC}$ and $CTAB_P$ are as previously defined.

Signal 266, which is representative of the calculated CTAB number for the product carbon black, is provided as an input to the controller 267. The controller 267 is also provided with a set point signal 268 which is representative of the desired CTAB number for the carbon black product. The controller 267, which is a digital implementation of a proportional-integral controller, compares signals 266 and 268 and provides signal 171 responsive to the difference between signals 266 and 268. Signal 171 is provided as an output control signal from computer means 100 and is utilized as has been previously described.

Signal 135, which is representative of the flow rate of the potassium containing feed flowing through conduit means 17 ($F_K$), is provided as a first input to the calculate flow rate of potassium block 271. The calculate flow rate of potassium block 271 is also provided with the set point signal 272 which is representative of the percentage of potassium in the potassium containing feed flowing through conduit means 17. Signal 135 is multiplied by signal 272 to provide signal 274 which is representative of the flow rate of the potassium flowing to the carbon black reactor. Signal 274 is provided as an input to the predicted DPB calculation for production carbon black block 231.

Signals 144 and 149, which are respectively representative of the temperature and flow rate of the quench fluid flowing through conduit means 21, are provided as inputs to the calculate flow at standard conditions block 276. Signals 144 and 149 are utilized to calculate the flow rate of the quench fluid at standard conditions ($F_Q$) utilizing equation (XI):

$$F_Q = (F_{MEAS})\left(\sqrt{\frac{T_{STD}}{T_{MEAS}}}\right) \quad \text{(XI)}$$

where $F_{MEAS}$, $T_{STD}$ and $T_{MEAS}$ are as previously defined.

Signal 277, which is representative of the flow rate of the quench fluid flowing through conduit means 21 at standard conditions, is provided as an input to the predicted DBP calculation for production carbon black block 231.

The predicted DBP calculation for production carbon black block 231 is also provided with the set point signals 261 and 281. Signal 261 is representative of the length of the carbon black reactor 11. Signal 281 is representative of the location of the feed nozzle. Signals 234, 227, 274, 277, 261 and 281 are utilized to calculate the DBP number for the production carbon black utilizing equation (XII):

$$DBP = a + (b)(F_A) + (c)(F_F) + (d)(L) + (e)(F_Q) - (f)(N) + (g)(\exp^{(h)(FK)}) + (i)(L)(N) + (j)(F_A^2) \quad \text{(XII)}$$

where
- $DBP_P$ = DBP number for production carbon black;
- $F_Q$ = flow rate of the quench fluid;
- N = location of the feed nozzle;
- $F_K$ = the flow rate of potassium to the reactor;
- a, b, c, d, e, f, g, h, i and j = constants; and
- $F_A$, $F_F$ and L are as previously defined.

The constants a-j are determined by making a test run in which the DBP number of the carbon black product is measured and then determining the constants a-j based on a linear regression analysis. Signal 285, which is representative of the DBP number for the production carbon black, is supplied as an input to the calculate DBP number for carbon black product block 286. Signal 287, which is representative of the measured DBP number for the rerun carbon black ($DBP_R$), is also supplied as an input to the calculate DBP for carbon black product block 286. The value of signal 287 is determined by laboratory measurement of the DBP number for the rerun carbon black. Signals 285, 255, 251, and 287 are utilized to calculate the DBP number for the carbon black product ($DBP_{PROD}$) utilizing equation (XIII):

$$DBP_{PROD} = \left(\frac{F_{RC}}{F_{RC} + F_{PC}}\right)(DBP_R) + \left(\frac{F_{PC}}{F_{RC} + F_{PC}}\right)(DBP_P) \quad \text{(XIII)}$$

where
$DBP_{PROD}$, $F_{RC}$, $F_{PC}$, $DBP_R$ and $DBP_P$ are as previously defined.

Signal 291, which is representative of the calculated DBP number for the carbon black product, is supplied as an input to the controller 292. The controller 292 is also provided with a set point signal 293 which is representative of the desired DBP number for the carbon black product. The controller 292, which is a digital implementation of a proportional-integral controller, compares signals 291 and 293 and provides signal 181 which is responsive to the difference between signals 291 and 293. Signal 181 is supplied as a control output signal from the computer means 100 and is utilized as has been previously described.

The invention has been described in terms of a preferred embodiment as is illustrated in FIGS. 1 and 2. Specific components which can be utilized in the practice of the invention as illustrated in FIG. 1 such as flow controllers 174, 184 and 167; temperature transducers 56, 71, 92 and 141; flow transducers 61, 81, 101, 131, 145 and 155; flow sensors 62, 82, 102, 132, 146 and 156; pneumatic control valves 186, 176 and 169; ammeter 161; amperage controller 164; and pressure transducers 76 and 96 are each well known commercially available control components such as are described at length in Perry's "Chemical Engineers Handbook", 4th Edition, Chapter 22, McGraw-Hill.

Analyzers transducers 121 and 111 are preferably the optichrom 2100 manufactured by Applied Automation, Inc., Bartlesville, Oklahoma. Density transducer 51 is preferably a Dynatrol Density Meter, manufactured by Automation Product, Inc. Dew point analyzer transducer 87 is preferably a Honeywell Dew Probe, Model No. SSP-129B021, manufactured by Honeywell. Computer means 100 is preferably an OPTROL 3600 manufactured by Applied Automation, Inc.

Also, for reasons of brevity and clarity, conventional auxiliary equipment such as pumps for feed and fuel gases, additional heat exchangers, additional measurement-control devices, and additional processing equipment required in carbon black production have not been included in the above description as they play no part in the explanation of the invention.

While the invention has been described in terms of the presently preferred embodiment, reasonable variations and modifications are possible, by those skilled in the art, within the scope of the described invention and the appended claims. For example, the basic control method illustrated in FIGS. 1 and 2 may frequently be used as a subsystem for a more comprehensive carbon black process control.

That which is claimed is:

1. A method for producing carbon black comprising the steps of:
    contacting hot combustion gases and a carbonaceous feed in a reaction zone to thereby convert said carbonaceous feed to a production carbon black;
    combining a rerun carbon black, having a CTAB number which does not meet predetermined specifications, with said production carbon black to thereby produce a combined carbon black product;
    establishing a first signal representative of the flow rate ($F_{PC}$) of said production carbon black;
    establishing a second signal representative of the flow rate ($F_{RC}$) of said rerun carbon black;
    establishing a third signal representative of the CTAB number ($CTAB_P$) of said production carbon black;
    establishing a fourth signal representative of the CTAB number ($CTAB_R$) of said rerun carbon black;
    establishing a fifth signal representative of the CTAB number ($CTAB_{PROD}$) of said combined carbon black product in response to said first, second, third and fourth signals;
    establishing a sixth signal representative of the desired CTAB number for said combined carbon black product;
    establishing a seventh signal responsive to the difference between said fifth signal and said sixth signal; and
    controlling the flow rate of said carbonaceous feed to said reaction zone in response to said seventh signal to thereby maintain a desired CTAB number for said combined carbon black product.

2. A method in accordance with claim 1 wherein said hot combustion gases are supplied by the combustion of a fuel and an oxygen containing gas.

3. A method in accordance with claim 2 wherein said step of establishing said first signal comprises:
    establishing an eighth signal representative of the flow rate of said oxygen containing gas;
    establishing a ninth signal representative of the flow rate of said carbonaceous feed;
    establishing a tenth signal representative of the flow rate of said fuel;

establishing an eleventh signal representative of an analysis of the carbon content in said fuel;

establishing a twelfth signal representative of the analysis of the carbon content in said carbonaceous feed;

establishing a thirteenth signal representative of the flow rate of carbon to said reaction zone in response to said eighth, ninth, tenth, eleventh and twelfth signals;

establishing a fourteenth signal representative of an analysis of the carbon in forms other than carbon black in the effluent flowing form said reaction zone; and establishing said first signal in response to said thirteenth and fourteenth signals.

4. A method in accordance with claim 1 additionally comprising the steps of:

supplying said combined carbon black product to a carbon black mixer;

supplying water to said carbon black mixer; and supplying the pelleted combined carbon black product from said carbon black mixer to a carbon black dryer.

5. A method in accordance with claim 4 wherein said step of establishing said second signal comprises:

establishing an eighth signal representative of the flow rate ($F_W$) of said water;

establishing a ninth signal representative of the percentage of water ($WT\%_W$) in said pelleted combined carbon black product;

multiplying said eighth signal and said ninth signal to establish a tenth signal representative of ($F_W$)($WT\%_W$); and subtracting said first signal from said signal to establish said second signal.

6. A method in accordance with claim 1 wherein said step of establishing said fifth signal comprises:

summing said first signal and said second signal to establish an eighth signal representative of $F_{RC}+F_{PC}$;

dividing said second signal by said eighth signal to produce a ninth signal representative of $F_{RC}/(F_{RC}+F_{PC})$;

multiplying said ninth signal by said fourth signal to produce a tenth signal representative of $(F_{RC}/(F_{RC}+F_{PC}))(CTAB_R)$;

dividing said first signal by said eighth signal to establish an eleventh signal representative of $F_{PC}/(F_{RC}+F_{PC})$;

multiplying said eleventh signal by said third signal to establish a twelfth signal representative of $(F_{PC}/(F_{RC}+F_{PC}))(CTAB_P)$; and summing said sixteenth signal and said eighteenth signal to establish said fifth signal.

7. A method in accordance with claim 1 wherein said rerun carbon black also has a DBP number which does not meet predetermined specifications.

8. A method in accordance with claim 7 comprising the additional steps of:

supplying potassium to said reaction zone;

establishing an eighth signal representative of the DBP number of said production carbon black;

establishing a ninth signal representative of the DBP number of said rerun carbon black;

establishing a tenth signal representative of DBP number of said combined carbon black product in response to said first, second, eighth and ninth signals;

establishing an eleventh signal representatives of the desired DBP number for said combined carbon black product;

comparing said tenth signal and said eleventh signal and establishing a twelfth signal responsive to the difference between said tenth signal and said eleventh signal; and controlling the flow rate of potassium to said reaction zone in response to said twelfth signal to thereby maintain a desired DBP number for said combined carbon black product.

9. A method in accordance with claim 8 wherein said step of establishing said tenth signal comprises:

summing said first signal and said second signal to establish a thirteenth signal representative of $F_{RC}+F_{PC}$;

dividing said second signal by said thirteenth signal to produce a fourteenth signal representative of $F_{RC}/(F_{RC}+F_{PC})$;

multiplying said fourteenth signal by said fourth signal to produce a fifteenth signal representative of $(F_{RC}/(F_{RC}+F_{PC}))(DBP_R)$;

dividing said first signal by said thirteenth signal to establish a sixteenth signal representative of $F_{PC}/(F_{RC}+F_{PC})$;

multiplying said sixteenth signal by said third signal to establish a seventeenth signal representative of $(F_{PC}/(F_{RC}+F_{PC}))(DBP_P)$; and summing said fifteenth signal and said seventeenth signal to establish said fifth signal.

10. A method for producing carbon black comprising the steps of:

contacting hot combustion gases, a carbonaceous feed and potassium in a reaction zone to therby convert said carbonaceous feed to a production carbon black;

combining a rerun carbon black, having a DBP number which does not meet predetermined specifications, with said production carbon black to thereby produce a combined carbon black product;

establishing a first signal representative of the flow rate ($F_{PC}$) of said production carbon black;

establishing a second signal representative of the flow rate ($F_{RC}$) of said rerun carbon black;

establishing a third signal representative of the DBP number ($DBP_P$) of said production carbon black;

establishing a fourth signal representative of the DBP number ($DBP_R$) of said rerun carbon black;

establishing a fifth signal representative of the DBP number ($DBP_{PROD}$) of said combined carbon black product in response to said first, second, third and fourth signals;

establishing a sixth signal representative of the desired DBP number for said combined carbon black product;

establishing a seventh signal responsive to the difference between said fifth signal and said sixth signal; and controlling the flow rate of potassium to said reaction zone in response to said seventh signal to thereby maintain a desired DBP number for said combined carbon black product.

11. A method in accordance with claim 10 wherein said hot combustion gases are supplied by the combustion of a fuel and an oxygen containing gas.

12. A method in accordance with claim 11 wherein said step of establishing said first signal comprises:

establishing an eighth signal representative of the flow rate of said oxygen containing gas;

establishing a ninth signal representative of the flow rate of said carbonaceous feed;

establishing a tenth signal representative of the flow rate of said fuel;

establishing an eleventh signal representative of an analysis of the carbon content in said fuel;

establishing a twelfth signal representative of the analysis of the carbon content in said carbonaceous feed;

establishing a thirteenth signal representative of the flow rate of carbon to said carbon black reactor in response to said eighth, ninth, tenth, eleventh and twelfth signals;

establishing a fourteenth signal representative of an analysis of the carbon in forms other than carbon black in the effluent flowing from said reaction zone; and establishing said first signal in response to said thirteenth and fourteenth signals.

13. A method in accordance with claim 10 additionally comprising the steps of:

supplying said combined carbon black product to a carbon black mixer;

supplying water to said carbon black mixer; and supplying the pelleted combined carbon black product from said carbon black mixer to a carbon black dryer.

14. A method in accordance with claim 13 wherein said step of establishing said second signal comprises:

establishing an eighth signal representative of the flow rate of said water ($F_W$);

establishing a ninth signal representative of the percentage of water in said pelleted combined carbon black product ($WT\%_W$);

multiplying said eighth signal and said ninth signal to establish a tenth signal representative of ($F_W$)($WT\%_W$); and subtracting said first signal from said tenth signal to establish said second signal.

15. A method in accordance with claim 10 wherein said step of establishing said fifth signal comprises:

summing said first signal and said second signal to establish an eighth signal representative of $F_{RC} + F_{PC}$;

dividing said second signal by said eighth signal to produce a ninth signal representative of $F_{RC}/(F_{RC}+F_{PC})$;

multiplying said ninth signal by said fourth signal to produce a tenth signal representative of $(F_{RC}/(F_{RC}+(F_{PC}))(DBP_R)$;

dividing said first signal by said eighth signal to establish an eleventh signal representative of $F_{PC}/(F_{RC}+F_{PC})$;

multiplying said eleventh signal by said third signal to establish a twelfth signal representative of $(F_{PC}/(F_{RC}+F_{PC}) (DBP_P)$; and summing said tenth signal and said twelfth signal to establish said fifth signal.

* * * * *